(12) United States Patent
Koschuh et al.

(10) Patent No.: US 9,120,061 B2
(45) Date of Patent: Sep. 1, 2015

(54) PROCESS FOR THE TREATMENT OF A STREAM OF SUBSTANCES

(75) Inventors: Werner Koschuh, Graz (AT); Stefan Kromus, Vienna (AT)

(73) Assignee: GRUENE-BIORAFFINERIE.AT GMBH, Raaba (AT)

( * ) Notice: Subject to any disclaimer, the term of this patent is extended or adjusted under 35 U.S.C. 154(b) by 937 days.

(21) Appl. No.: 12/517,518

(22) PCT Filed: Dec. 19, 2007

(86) PCT No.: PCT/AT2007/000571
§ 371 (c)(1), (2), (4) Date: Jul. 8, 2009

(87) PCT Pub. No.: WO2008/074042
PCT Pub. Date: Jun. 26, 2008

(65) Prior Publication Data
US 2010/0038246 A1 Feb. 18, 2010

(30) Foreign Application Priority Data
Dec. 19, 2006 (AT) .................................. A 2091/2006

(51) Int. Cl.
*B01D 61/44* (2006.01)
*B01D 61/42* (2006.01)
(Continued)

(52) U.S. Cl.
CPC .............. *B01D 61/44* (2013.01); *B01D 61/025* (2013.01); *B01D 61/027* (2013.01); *B01D 61/58* (2013.01);
(Continued)

(58) Field of Classification Search
CPC ............................................... C12P 7/40–7/58
USPC ........................................................ 435/139
See application file for complete search history.

(56) References Cited

U.S. PATENT DOCUMENTS 5,002,881 A * 3/1991 Van Nispen et al. .......... 435/139
5,635,071 A * 6/1997 Al-Samadi .................... 210/652
(Continued)

FOREIGN PATENT DOCUMENTS

DE 3812440 10/1989
DE 3812440 A1 * 10/1989 ............... A23B 7/10
(Continued)

OTHER PUBLICATIONS

English Translation of DE 3812440 A1.*
(Continued)

*Primary Examiner* — Keith Hendricks
*Assistant Examiner* — Salil Jain
(74) *Attorney, Agent, or Firm* — Lowe Hauptman & Ham, LLP

(57) ABSTRACT

A process for a stream of substances containing at least one valuable substance including (A) amino acids, (B) carboxylic acids, and (C) inorganic salts includes: (1) treating the stream by nanofiltration to obtain a retentate enriched with valuable substance (A); (2) treating the permeate of step (1) by electrodialysis in order to obtain a concentrate enriched with valuable substance (C); (3) treating the diluate of step (2) using a system (3) of two stages (4) and (5) which are directly or indirectly interconnected, wherein (4) one treatment is performed by reverse osmosis and (5) one treatment is performed by electrodialysis, whereby a concentrate enriched with valuable substance (B) is obtained, (6) at least a portion of the retentate of step (4) is directly or indirectly supplied to step (5) and (7) at least a portion of the diluate of step (5) is directly or indirectly supplied to step (4).

15 Claims, 2 Drawing Sheets

(51) Int. Cl.
  *B01D 61/02* (2006.01)
  *B01D 61/58* (2006.01)
  *C12P 7/40* (2006.01)
  *C12P 7/56* (2006.01)
  *C12P 7/42* (2006.01)

(52) U.S. Cl.
  CPC ... *C12P 7/40* (2013.01); *C12P 7/56* (2013.01); *B01D 61/422* (2013.01); *B01D 2317/025* (2013.01); *B03D 2203/003* (2013.01); *C12P 7/42* (2013.01)

(56) References Cited

U.S. PATENT DOCUMENTS

| | | | | |
|---|---|---|---|---|
| 5,681,728 | A | * | 10/1997 | Miao ............................. 435/136 |
| 5,766,439 | A | * | 6/1998 | Eyal et al. ..................... 204/524 |
| 6,875,839 | B2 | * | 4/2005 | Gerking et al. ............... 528/354 |
| 7,008,485 | B2 | * | 3/2006 | Heikkila et al. ............... 127/55 |
| 7,083,730 | B2 | * | 8/2006 | Davis ............................ 210/652 |
| 7,537,697 | B2 | * | 5/2009 | Koo et al. .................. 210/500.38 |
| 7,794,598 | B2 | * | 9/2010 | Zaitsev ......................... 210/605 |
| 2004/0033573 | A1 | * | 2/2004 | Norddahl et al. ............. 435/139 |

FOREIGN PATENT DOCUMENTS

| | | |
|---|---|---|
| DE | 3215818 | 12/1992 |
| DE | 4212187 | 4/1993 |
| DE | 4427478 | 2/1995 |
| EP | 0049055 | 4/1982 |
| EP | 0295591 | 6/1988 |
| EP | 0531864 | 3/1993 |

OTHER PUBLICATIONS

Hong Thang et al., "Detailed Investigation of an Electrodialytic Process During the Separation of Lactic Acid From a Complex Mixture", Journal of Membrane Science 249, 2005, pp. 173-182.

Koschuh et al., "Production of Leaf Protein Concentrate From Ryegrass (*Lolium perenne* x *multiflorum*) and Alfalfa (*Medicago sativa* Subsp. *sativa*). Comparison Between Heat Coagulation/Centrifugation and Ultrafiltration", Desalination 163, 2004, pp. 253-259.

Hong Thang et al., "Desalination of High Salt Content Mixture by Two-Stage Electrodialysis as the First Step of Separating Valuable Substances From Grass Silage", Desalination 162, 2004, pp. 343-353.

Koschuh et al., "Flux and Retention Behaviour of Nanofiltration and Fine Ultrafiltration Membranes in Filtrating Juice From a Green Biorefinery: A Membrane Screening", Journal of Membrane Science 261, 2005, pp. 121-128.

Hong Thang et al., "Electrodialysis Versus Chromatography for Desalting Silage Juice: Comparison of Both Processes with Regard to Energy Consumption", Journal of Membrane Science 256, 2005 pp. 78-88.

\* cited by examiner

PROCESS FOR THE TREATMENT OF A STREAM OF SUBSTANCES

CROSS-REFERENCE TO RELATED APPLICATIONS

The present Application is based on International Application No. PCT/AT2007/000571, filed on Dec. 19, 2007, which in turn corresponds to Austria Application No. A 2091/2006, filed on Dec. 19, 2006, and priority is hereby claimed under 35 USC §119 based on these applications. Each of these applications are hereby incorporated by reference in their entirety into the present application.

FIELD OF THE INVENTION

The present invention concerns a process for the treatment of a complex stream of substances containing several valuable substances of a different chemical nature.

BACKGROUND OF THE INVENTION

The problems associated with separating or treating complex streams of substances in order to enrich the various valuable substances contained therein arise particularly in the field of biogenically-based aqueous liquids, such as, for example, liquids from fermentation processes and in particular liquids obtained from silage.

Liquids obtained from whole-plant silage or silage from grassland biomass (such as, e.g., from grass, clover, alfalfa, herbs etc.) have for some time been regarded as interesting raw materials for the obtainment of fine chemicals. In the following, the term "grass silage" is used to represent all silages from grassland biomass.

In the context of the "Österreichisches Programm zur Entwicklung der Green Biorefinery [Austrian Programme for the Development of Green Biorefinery]" it has been shown that valuable substances accumulating during the silage process of, e.g., grass, such as lactic acid and proteinogenic amino acids, convert the biogenic raw material grass into a potentially interesting source for obtaining such valuable substances. This concept is interesting particularly because of the possibility of using an inexpensive and, in addition, renewable raw material.

It is, however, problematic that the complex streams of substances accumulating, for example, with the grass silage comprise a plurality of valuable substances of a varying chemical nature the separation of which is difficult.

SUMMARY OF THE INVENTION

The embodiments of the present invention deals in particular with complex streams of substances which contain in each case at least one valuable substance from the groups of
  (A) amino acids
  (B) carboxylic acids different from amino acids and comprising from 1 to 5 C-atoms, and
  (C) inorganic salts.

Mixtures of these three groups of valuable substances can be found in the already mentioned liquids from grass silage. These are indicated below by the summarizing term "silage liquid".

Hong Thang et al., J. Membr. Sc. 249 (2005) 173-182 describe the application of an electrodialytic process for the separation of lactic acid from a complex liquid from grass silage.

Koschuh et al., Desalination 163 (2004) 254-259 describe the application of ultrafiltration for liquids from pressed grass and alfalfa for obtaining a concentrate rich in protein.

Hong Thang et al., Desalination 162 (2004) 343-353 describe a two-stage electrodialytic process for the treatment of grass silage. An extensive desalination of the stream of substances occurs in the first step of said process, in the second step, lactic acid is enriched.

Koschuh et al., J. Membr. Sc. 261 (2005) 121-128 examine the flux and retention behavior of nanofiltration and fine ultrafiltration membranes during the filtration of a silage liquid.

Hong Thang et al., J. Membr. Sc. 256 (2005) 78-88 compare methods of electrodialysis to chromatographic methods with regard to their effectiveness in desalinating a silage liquid.

In the published prior art, solely the enrichment of one or at best two of the above-mentioned groups of valuable substances (A), (B) and (C) has so far been described.

Furthermore, the known methods are characterized by a diffuse selectivity, in particular between amino acids (A) and organic acids (B). A series of such processing steps with a diffuse separation in each case results in low yields, i.e., in side flows with low concentrations of the valuable substance. In the majority of cases, such side flows cannot be used commercially and are thus waste.

If, for example, such a process series is carried out with nanofiltration steps, huge amounts of process water are additionally required for flushing out the undesired accompanying substances (B) and (C).

If such a process series is carried out using methods of electrodialysis, the electrodialysis has to be performed partly with adverse concentrations of valuable substances in order to ensure high yields. Such adverse or low concentrations of valuable substances, respectively, entail increased losses and an unintentional transfer of accompanying substances.

The embodiments of the present invention are directed to providing a process by means of which all groups of valuable substances (A), (B) and (C) contained in a complex stream of substances, particularly in a silage liquid, can be enriched at a concentration sufficient for further processing.

The above is achieved by a process for the treatment of a stream of substances which contains at least one valuable substance from each of the following groups
  (A) amino acids
  (B) carboxylic acids different from amino acids and comprising from 1 to 5 C-atoms, and
  (C) inorganic salts,
which process comprises the following steps:
  (1) treatment of the stream of substances by nanofiltration in order to obtain a retentate enriched with valuable substance (A)
  (2) treatment of the permeate of step (1) by electrodialysis in order to obtain a concentrate enriched with valuable substance (C)
  (3) treatment of the diluate of step (2) using a system (3) of two stages (4) and (5) which are directly or indirectly interconnected, wherein
  (4) one treatment is performed by reverse osmosis and
  (5) one treatment is performed by electrodialysis, whereby a concentrate enriched with valuable substance (B) is obtained
  (6) at least a portion of the retentate of step (4) is directly or indirectly supplied to step (5)
  (7) at least a portion of the diluate of step (5) is directly or indirectly supplied to step (4).

Thus, a nanofiltration step is initially performed in which a retentate enriched with valuable substance (A), i.e., amino acids, is obtained. The retentate is discharged from the total process.

Using a method of electrodialysis practiced under appropriate conditions, a concentrate enriched with valuable substance (C), i.e., the inorganic salts, can be attained from the permeate of the nanofiltration of step (1). The concentrate is likewise discharged from the total process.

The diluate of electrodialysis (2) is supplied to a system (3) comprising a treatment by reverse osmosis (5) and by electrodialysis (5), with the stages (4) and (5) being directly or indirectly connected to each other.

Thereby, at least a portion of the retentate of step (4) is directly or indirectly supplied to step (5) and at least a portion of the diluate of step (5) is directly or indirectly supplied to step (4).

A reconcentration of the diluate of step (2) is effected by means of the reverse osmosis treatment in step (4).

In the electrodialysis treatment (5), a concentrate enriched with valuable substance (B), i.e., the organic carboxylic acids, is obtained under appropriate conditions.

By directly or indirectly recycling the diluate from the electrodialysis of step (5) back to the reverse osmosis (step (4)), a permanent further enrichment of the valuable substances (B) is achieved.

In an embodiment of the process according to the invention, the steps (4) and (5) are connected in a circuit, wherein at least a portion of the retentate of step (4) is supplied to step (5) and at least a portion of the diluate of step (5) is returned to step (4).

Direct cycling between steps (4) and (5) is thereby achieved.

In a further embodiment of the process according to the invention, the diluate of step (2) is conveyed into a balancing reservoir from which both step (4) and step (5) are fed and into which at least a portion of the retentate of step (4) and a portion of the diluate of step (5) are returned.

Indirect cycling between steps (4) and (5) via the balancing reservoir is thereby achieved.

In the process according to the invention, the steps (4), (5), (6) and (7), i.e., the above-described cycling, are preferably carried out in a steady-state operation.

Particularly preferably, all the steps (1) to (7) are carried out in a steady-state operation.

The nanofiltration provided in step (1) of the process according to the invention is preferably a two- or multi-stage nanofiltration, wherein preferably at least one of the stages carried out after the first stage is configured as a diafiltration. Particularly, if more than two stages are provided, all the stages provided after the first stage can be configured as a diafiltration.

Preferably, in the process according to the invention, a portion of the permeate of step (4) and/or at least a portion of the diluate of step (5) is/are supplied to the nanofiltration in step (1).

In particular, the entire permeate of step (4) as well as the portion of the diluate of step (5) which optionally is not recycled to step (4) can be supplied to the nanofiltration in step (1), resulting in a practically closed circuit from which only the streams of substances enriched with valuable substances (A), (B) and (C) are discharged.

If, as is preferably provided, nanofiltration is performed in two or more stages, the permeate of step (4) or a portion thereof, respectively, and/or the portion of the diluate of step (5) is/are preferably supplied to the second stage of nanofiltration, particularly to a diafiltration stage.

In the nanofiltration of step (1), a membrane is preferably used which exhibits a high permeability towards monovalent inorganic salts and, compared with this, a lower permeability towards divalent inorganic salts.

The material of the membrane used can preferably be selected from the group consisting of permanently hydrophilized polyethersulfone, ceramics, in particular $TiO_2$, polyamide and semiaromatic piperazine polyamide. The cut-off point ("nominal molecular weight cut off"—NMWCO) ranges from 100 to 4000 Da, preferably from 100 to 1000 Da, particularly preferably from 150 to 300 Da.

The following materials are, for example, suitable as membranes for the nanofiltration process of stage (1):

|  | Manufacturer | | | | | |
| --- | --- | --- | --- | --- | --- | --- |
|  | Nadir PES 10 | Nadir N30F | Koch MPF36 | Nadir PES004H | Inocermic/D Inocermic | Tami Tami-1k |
| Material | Ph-PES | Ph-PES | unknown | Ph-PES | $TiO_2$ | $TiO_2$ |
| NMWCO (Da) | 1000 | 150-350 | 1000 | 4000 | 500 | 1000 |
| Pure water permeability at 20° C. ($Lh^{-1}m^{-2}MPa^{-1}$) | $95^a$ | $13^a$ | $60^a$ | $77^b$ | $131^b$ | $240^b$ |
| pH-operating range | 0-14 | 0-14 | 1-13 | 0-14 | 0-14 | 0-14 |
| Maximum temperature (° C.) | 95 | 95 | 70 | 95 | >100 | >100 |
| Classification | NF | NF | NF | UF | NF | UF |

|  | Manufacturer | | | |
| --- | --- | --- | --- | --- |
|  | GE Osmonics DL | GE Osmonics DK | Hydronautics NTR 7450 | Dow Deutschland NF 200 |
| Material | polyamide | polyamide | Ph-PES | semi-aromatic piperazine polyamide |

-continued

| | | | | |
|---|---|---|---|---|
| NMWCO (Da) | 150-300 | 150-300 | | |
| Pure water permeability at 20° C. (Lh$^{-1}$m$^{-2}$MPa$^{-1}$) | 76 | ~70 | 130 | 110 |
| pH-operating range | 2-11 | 2-11 | 2-11 | 3-10 |
| Maximum temperature (° C.) | | | | |
| Classification | NF | NF | NF | NF | ph-PES: permanently hydrophilized polyethersulfone;
NMWCO: nominal molecular weight cut off
$^a$at 1 MPa (10 bar); 20° C.
$^b$at 0.2 MPa (2 bar); 20° C.

In particular monopolar electrodialytic processes comprising a preferred transfer of chloride ions are suitable for the method of electrodialysis of step (2).

The following membrane types are, for example, suitable as membrane materials for step (2):

| Membrane manufacturer | Type |
|---|---|
| Neosepta | XCMX, AMX |
| Ionics | CR69EXMP/AR103QDP |

In step (4) of the process according to the invention, dense reverse osmosis membranes are preferably used in a spiral structure.

The reverse osmosis of step (4) is preferably performed using hydrophilic membranes having high water permeability, with a high retention of inorganic salts such as sodium chloride.

Preferably a monopolar electrodialysis is carried out in step (5) of the process according to the invention. The pH-value during the electrodialysis preferably ranges between 2 and 5.

The stream of substances to be treated by the process according to the invention typically has a pH-value of from 1 to 4.5.

The valuable substance of group (A) preferably is one or several proteinogenic amino acid(s), e.g. leucine.

The valuable substance of group (B) is in particular lactic acid.

The valuable substance of group (C) particularly is one or several inorganic salt(s) from the group of chloride salts, in particular sodium chloride, potassium chloride and/or mixtures thereof.

The stream of substances to be treated is in particular an aqueous liquid based on a biogenic source, preferably a liquid obtained from silage of, for example, grass, clover, alfalfa, herbs as well as mixtures thereof.

A plant serves for carrying out the process according to the invention, comprising
 a nanofiltration installation 1
 a first electrodialysis installation 2,
 a conduit 11 for conveying permeate from the nanofiltration installation 1 to the first electrodialysis installation 2,
 a system 3 made up of units 4 and 5 directly or indirectly connected to each other, wherein
 unit 4 is a reverse osmosis installation and—unit 5 is a second electrodialysis installation,
 a conduit 21 for conveying diluate from the first electrodialysis installation 2 into the system 3,
 a conduit 41 by means of which at least a portion of the retentate from the reverse osmosis installation 4 is directly or indirectly conveyed to the second electrodialysis installation 5 and
 a conduit 51 by means of which at least a portion of the diluate from the second electrodialysis installation is directly or indirectly conveyed to the reverse osmosis installation 4.

In an embodiment of the plant according to the invention, the conduit 41 conveys the retentate from the reverse osmosis installation 4 directly to the second electrodialysis installation 5.

In a further embodiment of the plant according to the invention, the conduit 51 conveys the diluate from the second electrodialysis installation 5 directly to the reverse osmosis installation 4.

Direct cycling between the units 4 and 5 is thereby achieved.

In an alternative embodiment of the plant according to the invention, a balancing reservoir 31 is provided into which the conduit 21 for the diluate from the first electrodialysis installation 2 runs, from which both the reverse osmosis installation 4 and the second electrodialysis installation 5 are fed and to which the conduit 41 for the retentate from the reverse osmosis installation 4 and the conduit 51 for the diluate from the second electrodialysis installation return.

Indirect cycling between the units 4 and 5 is thereby achieved.

In the plant according to the invention, the nanofiltration installation preferably has a multi-stage design, wherein particularly preferably at least one of the stages carried out after the first stage is configured as a diafiltration installation.

Furthermore, a conduit 42 for returning permeate from the reverse osmosis installation 4 to the nanofiltration installation 1, particularly preferably to an optionally provided second or further stage of the nanofiltration installation 1, is preferably provided.

Likewise, a conduit 52 for returning diluate from the second electrodialysis installation 5 to the nanofiltration installation 1, particularly preferably to the first stage of the nanofiltration installation 1, can preferably be provided.

The process according to the invention is characterized by the following advantages:

When considered separately, each partial process of the process according to the invention functions at a separation performance (valuable substance in the input relative to valuable substance in the separate output flow) of from 0.1 to 0.95. However, back-coupling with the other processing steps will result in overall separation performances that are clearly above 0.5.

In the process according to the invention, no waste flow accumulates particularly with a complete cycling also of the permeate from the reverse osmosis installation (step (4)) and of the diluate from the second electrodialysis installation (step (5)).

All three product streams ((A), (B) and (C)) are concentrated with regard to the incoming stream of substances.

The steps of the electrodialysis (2, 5) and of the reverse osmosis (4) interact with one another. A separation of inorganic salts (step (2)) and a separation of organic acids (step (5)) result in a reduced osmotic pressure, which increases the efficiency of the reverse osmosis in step (4). Vice versa, the reconcentration of valuable substances by reverse osmosis leads to an increase in efficiency of the electrodialysis in step (5).

Reverse osmosis (4) and nanofiltration (1) interact with one another. Water from the reverse osmosis is preferably admixed to the second nanofiltration stage in order to enable the valuable substances (B) and (C) to be flushed out preferably in a diafiltration step.

Nanofiltration (1) and electrodialysis (5) interact with one another. Nanofiltration alone results in an enrichment of amino acids in the retentate with a partial separation of organic acids into the permeate. With electrodialysis alone, organic acids are separated from a solution rich in amino acids only involving substantial losses of amino acids. In the process according to the invention, the nanofiltration (1) can retain a large part of the amino acids, whereas the electrodialysis (2) can neatly separate the organic acid continuously at suitable mass ratios ((B)>>(A)). By recycling a partially desalinated medium (after steps (2) and (5)), the amino acid losses from the nanofiltration (1) are compensated for and the throughput of lactic acid is increased such that the separation capacity of the electrodialysis will affect an essential part of the incoming amount of the organic acid (B), when the total process is taken into consideration.

The total process is designed for the benefit of the amino acids (valuable substance (A)). A contamination of the valuable substance (A) with traces of valuable substance (B) is tolerated, whereas the aim is to achieve a maximum yield of amino acids (A).

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein.

DETAILED DESCRIPTION OF THE EMBODIMENTS

Figure 1:
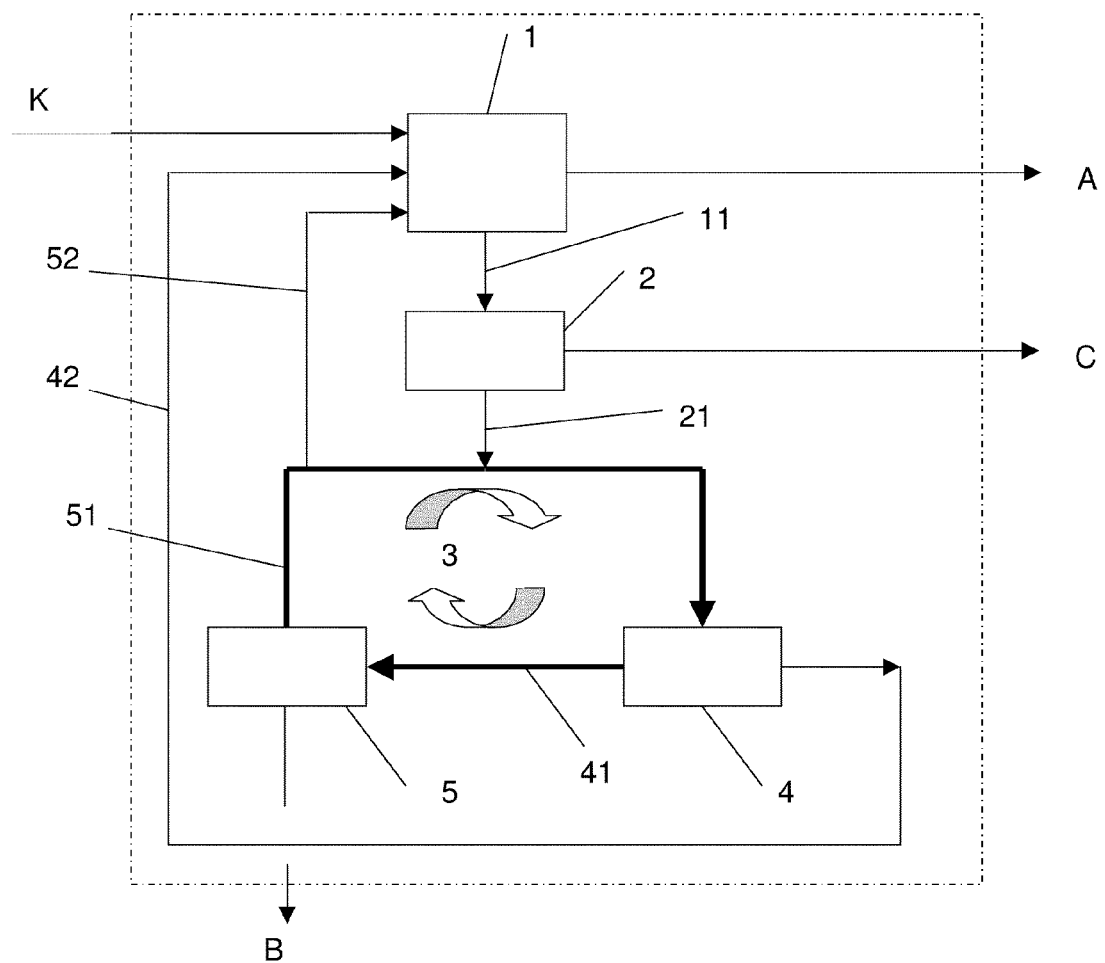
FIG. 1 schematically shows the design of an embodiment of the process according to the invention and of the plant according to another embodiment of the invention.

According to FIG. 1, a complex stream of substances K is supplied to a nanofiltration installation 1 and is nanofiltered there. The result is a retentate A enriched with amino acids which is discharged from the process.

The permeate of nanofiltration 1, which contains inorganic salts (C) and organic acids (B), is supplied via conduit 11 to a first electrodialysis installation 2. The concentrate of electrodialysis is enriched with inorganic salts and is discharged as a stream of valuable substances C.

The diluate of the first electrodialysis installation is supplied via conduit 21 to a system 3 including a reverse osmosis installation 4 and a second electrodialysis installation 5.

The retentate side of the reverse osmosis installation 4 is connected via a conduit 41 to the electrodialysis installation 5. On the diluate side, a conduit 51 returns from the electrodialysis installation 5 to the reverse osmosis installation 4.

The concentrate from the electrodialysis installation 5 is enriched with organic acids, e.g., lactic acid, and is discharged as a stream of valuable substances B. Via conduit 51, the diluate from the electrodialysis installation 5 is at least partially recycled back to the reverse osmosis installation 4. As illustrated, the supply conduit 21 can, for example, run into the conduit 51, however, the conduit 21 can also lead directly to the reverse osmosis installation 4.

At least a portion of the permeate from the reverse osmosis installation 4 is conveyed through the conduit 42 of the nanofiltration installation, particularly as a diafiltration water.

Likewise, at least a portion of the diluate from the second electrodialysis installation 5 can be returned via the conduit 52 of the nanofiltration installation 1.

Figure 2:
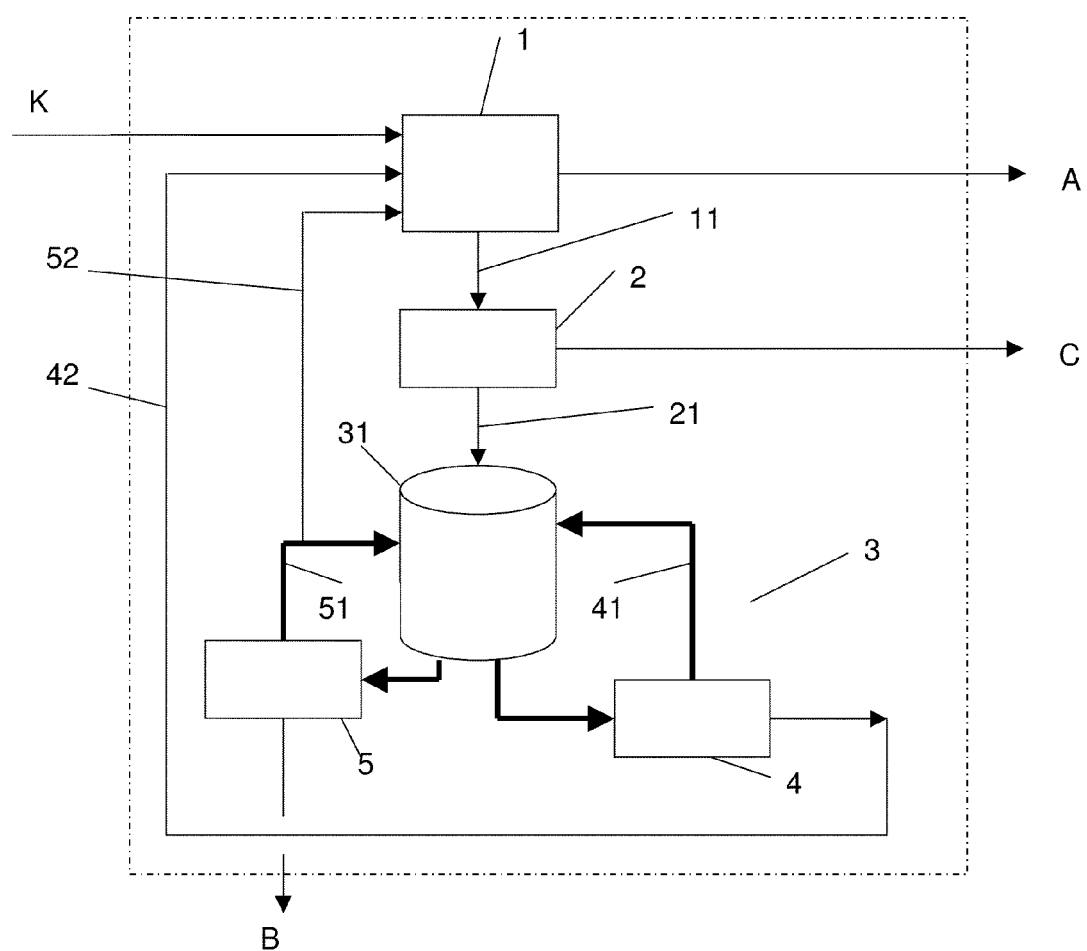
FIG. 2 schematically shows the design of an alternative embodiment of the process according to the invention and of the plant according to the invention.

In the embodiment illustrated in FIG. 2, a recipient vessel 31 is provided into which the conduit 21 for the diluate from the first electrodialysis installation 2 runs.

Starting from the recipient vessel 31, both the reverse osmosis installation 4 and the electrodialysis installation 5 are fed. Via conduit 41, the retentate of reverse osmosis 4 is fed back into the recipient vessel 31. Likewise, at least a portion of the diluate of electrodialysis 5 is fed back into the recipient vessel 31 via conduit 51.

EXAMPLES

Example 1

20 g L-lactic acid (90%), 30 g potassium lactate (50%), 3 g L-leucine and 10 g potassium chloride are dissolved in water and diluted to 1 kg.

The solution thus obtained has the following concentrations:

27.4 g/L lactic acid
3.0 g/L L-leucine
11.3 g/L potassium
4.8 g/L chloride

The solution is nanofiltered in a batch cell to a volume concentration factor of 2. 500 g of permeate and 500 g of concentrate accumulate.

The concentrations in the permeate are as follows:

19.2 g/L L-lactic acid
0.2 g/L L-leucine
9.0 g/L potassium
4.5 g/L chloride

The concentrations in the concentrate are as follows:
35.6 g/L L-lactic acid
5.9 g/L L-leucine
13.6 g/L potassium
5.0 g/L chloride Example 2

20 g L-lactic acid (90%), 30 g potassium lactate (50%), 3 g L-glycine and 10 g potassium chloride are dissolved in water and diluted to 1 kg.

The solution thus obtained has the following concentrations:
27.4 g/L lactic acid
3.0 g/L L-glycine
11.3 g/L potassium
4.8 g/L chloride The solution is nanofiltered in a batch cell to a volume concentration factor of 2. 500 g of permeate and 500 g of concentrate accumulate.

The concentrations in the permeate are as follows:
19.2 g/L L-lactic acid
0.9 g/L L-glycine
9.0 g/L potassium
4.5 g/L chloride The concentrations in the concentrate are as follows:
35.6 g/L L-lactic acid
5.1 g/L L-glycine
13.6 g/L potassium
5.0 g/L chloride Example 3

200 g L-lactic acid (90%), 300 g potassium lactate (50%), 30 g L-leucine and 100 g potassium chloride are dissolved in water and diluted to 10 kg.

The solution thus obtained has the following concentrations:
27.4 g/L lactic acid
3.0 g/L L-leucine
11.3 g/L potassium
4.8 g/L chloride The solution is nanofiltered in a nanofiltration installation to a volume concentration factor of 2.5 kg of permeate and 5 kg of concentrate accumulate.

The concentrations in the permeate are as follows:
19.2 g/L L-lactic acid
0.2 g/L L-leucine
9.0 g/L potassium
4.5 g/L chloride The concentrations in the concentrate are as follows:
35.6 g/L L-lactic acid
5.9 g/L L-leucine
13.6 g/L potassium
5.0 g/L chloride Example 4

2 kg of the permeate of Example 3 is used as a charge on the feed side of a monopolar electrodialysis. On the concentrate side, 1 kg of water is fed. Electrodialysis is stopped upon achieving a conductivity value of 6.5 on the concentrate side.

Concentrations on the feed side (diluate):
18.2 g/L L-lactic acid
0.2 g/L L-leucine
4.6 g/L potassium
0.9 g/L chloride The concentrations in the concentrate are as follows:
0.9 g/L L-lactic acid
0.0 g/L L-leucine
8.9 g/L potassium
7.2 g/L chloride Example 5

Reverse Osmosis of the Diluate of Example 4

2 kg of electrodialysis diluate of Example 4 is nanofiltered in a reverse osmosis cell to a volume concentration factor of 2.1000 g of permeate and 100 g of concentrate accumulate.

The concentrations in the permeate are as follows:
0.9 g/L L-lactic acid
0.0 g/L L-leucine
0.2 g/L potassium
0.1 g/L chloride The concentrations in the concentrate are as follows:
35.6 g/L L-lactic acid
0.4 g/L L-leucine
9.0 g/L potassium
1.7 g/L chloride Example 6

Electrodialysis of Reverse Osmosis Concentrate

Extraction of Lactic Acid 1 kg of the reverse osmosis concentrate of Example 5 is used as a charge on the feed side of a monopolar electrodialysis. On the concentrate side, 1 kg of water is fed.

After 67% of the lactic acid has been transferred, the experiment is stopped.

The concentrations on the feed side are as follows (diluate):
11.7 g/L L-lactic acid
0.4 g/L L-leucine
2.3 g/L potassium
0.3 g/L chloride The concentrations in the concentrate are as follows:
23.8 g/L L-lactic acid
0.0 g/L L-leucine
6.7 g/L potassium
1.4 g/L chloride Example 7

100 kg per hour of an aqueous solution (K) having a composition according to Example 1 are treated in a process chain constructed according to the invention (see FIG. 2).

Nanofiltration 1 is operated as a two-stage process. Diluate from the electrodialysis 5 and reverse osmosis permeate (water) from stage 4 are returned via conduits 42 and 52 to the first stage of nanofiltration. In addition, a portion of the reverse osmosis permeate of stage 4 is returned to the second stage of nanofiltration.

The concentration of lactic acid is adjusted on the feed side via the recycled amounts. In the first stage, a concentration of lactic acid of 25 g/L is achieved, in the second stage, a concentration of lactic acid of 11 g/L is achieved.

The permeate from both nanofiltration stages is merged and electrodialyzed (2). The ion transport capacity of the electrodialysis is configured such that the amount of ions separated can be controlled by varying the current intensity. The result is a preferred transport of potassium chloride.

The partially desalinated diluate is collected in a container 31. The container 31 is connected to the reverse osmosis installation 4 and the second electrodialysis installation 5 via circulation pumps. Reconcentration of the ingredients occurs according to the permeate output of the reverse osmosis installation. Discharge of salts, in particular of potassium lactate and hydrogen ions, occurs according to the ion transport capacity of the electrodialysis installation.

By adjusting the permeate output of the reverse osmosis installation 4 (enhancement by pressure increase), a concentration of lactic acid of 22 g/L, which is suitable for the electrodialysis, is adjusted.

A stream of nanofiltration concentrate (70 kg/h) enriched with leucine (A) (4.2 g/kg) is obtained.

A stream of electrodialysis concentrate (20 kg/h) enriched with lactic acid (B) (96 g/kg) is obtained.

A stream of electrodialysis concentrate (2 kg/h) enriched with potassium chloride (C) (76.4 g/kg) is obtained.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by definition contained in the appended claims and equivalents thereof.

The invention claimed is:

1. A process for the treatment of a stream of substances which contains at least one substance from each of the following groups:
   (A) amino acids;
   (B) carboxylic acids different from amino acids and having from 1 to 5 C-atoms; and
   (C) inorganic salts;
   wherein the stream of substances derives from silage liquids, and which process comprises the steps of:
   (1) treating the stream of substances by a two- or multi-stage nanofiltration, wherein at least one of the stages carried out after the first stage is configured as a diafiltration, and obtaining a retentate enriched with substance (A);
   (2) treating the permeate of step (1) by a first electrodialysis and obtaining a concentrate enriched with substance (C);
   (3) treating the diluate of step (2) by reverse osmosis and a second electrodialysis, wherein at least a portion of the retentate of the reverse osmosis is supplied to the second electrodialysis, and at least a portion of the diluate of the second electrodialysis is supplied to the reverse osmosis, and wherein at least a portion of the permeate of the reverse osmosis and at least a portion of the diluate of the second electrodialysis are supplied to the two- or multi-stage nanofiltration; and
   (4) obtaining a concentrate enriched with substance (B) in the second electrodialysis.

2. The process according to claim 1, wherein the reverse osmosis and the second electrodialysis are connected in a circuit, wherein at least a portion of the retentate of the reverse osmosis is supplied to the second electrodialysis and at least a portion of the diluate of the second electrodialysis is returned to the reverse osmosis.

3. The process according to claim 1, wherein the diluate of step (2) is conveyed into a balancing reservoir from which both the reverse osmosis and the second electrodialysis are fed and into which at least a portion of the retentate of the reverse osmosis and a portion of the diluate of the second electrodialysis are returned.

4. The process according to claim 1, wherein the steps (3) and (4) are carried out in a steady-state operation.

5. The process according to claim 1, wherein all the steps (1) to (4) are carried out in a steady-state operation.

6. The process according to claim 1, wherein step (1) comprises two or more treatments by nanofiltration.

7. The process according to claim 1, wherein at least a portion of the permeate of the reverse osmosis and/or at least a portion of the diluate of the second electrodialysis is/are supplied to the nanofiltration in step (1).

8. The process according to claim 1, wherein, in step (1), a membrane is used which exhibits a high permeability towards inorganic salts of monovalent ions and, compared with this, a lower permeability towards inorganic salts of divalent ions.

9. The process according to claim 8, wherein the material of the membrane used is selected from the group consisting of permanently hydrophilized polyethersulfones, ceramics, polyamides, and semiaromatic piperazine polyamides.

10. The process according to claim 1, wherein the second electrodialysis is configured as a monopolar electrodialysis.

11. The process according to claim 1, wherein the stream of substances to be treated has a pH-value of from 1 to 4.5.

12. The process according to claim 1, wherein the substance of group (A) is one or several amino acid(s) selected from the group consisting of proteinogenic amino acids.

13. The process according to claim 1, wherein the substance of group (B) is lactic acid.

14. The process according to claim 1, wherein the substance of group (C) is one or several inorganic salt(s) from the group of chloride salts.

15. The process according to claim 1, wherein the stream of substances to be treated is an aqueous liquid based on a biogenic source.

* * * * *